(12) United States Patent
Sweeney et al.

(10) Patent No.: US 12,201,307 B2
(45) Date of Patent: *Jan. 21, 2025

(54) ASSEMBLIES, SYSTEMS, AND METHODS FOR A NEUROMONITORING DRILL BIT

(71) Applicant: NuVasive, Inc., San Diego, CA (US)

(72) Inventors: Thomas Sweeney, San Diego, CA (US); John Love, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/584,407

(22) Filed: Feb. 22, 2024

(65) Prior Publication Data
US 2024/0188967 A1  Jun. 13, 2024

Related U.S. Application Data

(63) Continuation of application No. 17/497,133, filed on Oct. 8, 2021, now Pat. No. 11,931,052.

(51) Int. Cl.
*A61B 17/16* (2006.01)
*A61B 17/00* (2006.01)
*A61B 90/00* (2016.01)

(52) U.S. Cl.
CPC ...... *A61B 17/1633* (2013.01); *A61B 17/1615* (2013.01); *A61B 2017/00026* (2013.01); *A61B 2090/036* (2016.02); *A61B 2090/08021* (2016.02)

(58) Field of Classification Search
CPC ............... A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1662; A61B 17/1671
See application file for complete search history.

(56) References Cited

U.S. PATENT DOCUMENTS

| | | | | |
|---|---|---|---|---|
| 5,667,509 | A * | 9/1997 | Westin | A61B 17/1633 606/80 |
| 7,141,074 | B2 * | 11/2006 | Fanger | A61B 17/1757 606/80 |
| 8,092,457 | B2 * | 1/2012 | Oettinger | A61B 17/1626 606/80 |
| 8,374,673 | B2 * | 2/2013 | Adcox | A61B 90/36 600/410 |
| 8,518,065 | B2 * | 8/2013 | Shores | A61B 17/162 606/205 |

(Continued)

*Primary Examiner* — Eric S Gibson

(57) ABSTRACT

Assemblies, systems, and methods are directed at a neuromonitoring bone drill bit. The assembly may include a surgical bone drill bit, a neuromonitoring connection in electrical communication with the drill bit, and a shield extending over a distal end of the drill bit. The shield may be configured to withdraw proximally as the drill bit is advanced into a subject's bone. The assembly may be connected to a surgical drill and used in a surgical spinal procedure. In operation, the assembly may be advanced to a subject's bone at a surgical site and the drill bit may rotate into the subject's bone. In response, the shield may engage the bone and the drill bit may be advanced with respect to the shield. The shield may electrically insulate tissue from electrical current passing through the drill bit as it is inserted at the surgical site.

18 Claims, 12 Drawing Sheets

(56) References Cited

U.S. PATENT DOCUMENTS

| | | | | |
|---|---|---|---|---|
| 8,523,873 B2* | 9/2013 | Bharadwaj | ......... | A61B 17/1757 |
| | | | | 600/554 |
| 8,936,626 B1* | 1/2015 | Tohmeh | ............. | A61B 17/1615 |
| | | | | 606/279 |
| 9,155,545 B2* | 10/2015 | Prescott | ............. | A61B 17/1615 |
| 9,237,906 B2* | 1/2016 | Janssens | ............ | A61B 17/1633 |
| 9,801,668 B1* | 10/2017 | Ferree | ................ | A61B 17/7092 |
| 10,869,677 B2* | 12/2020 | Sallaz | .................. | A61B 5/4893 |
| 11,931,052 B2* | 3/2024 | Sweeney | ................ | A61B 90/04 |
| 2004/0059317 A1* | 3/2004 | Hermann | ........... | A61B 17/1633 |
| | | | | 606/1 |
| 2017/0056116 A1* | 3/2017 | Kostrzewski, Phd | ... | B25J 19/06 |
| 2017/0348062 A1* | 12/2017 | Sweeney | ................ | A61B 34/32 |
| 2019/0350597 A1* | 11/2019 | Akbarian | ............... | A61B 17/24 |
| 2023/0112058 A1* | 4/2023 | Sweeney | ............ | A61B 17/1615 |
| | | | | 606/80 |
| 2024/0188967 A1* | 6/2024 | Sweeney | ............ | A61B 17/1633 |

\* cited by examiner

ASSEMBLIES, SYSTEMS, AND METHODS FOR A NEUROMONITORING DRILL BIT

CROSS-REFERENCE TO RELATED APPLICATION(S)

The present application is a continuation application of U.S. patent application Ser. No. 17/497,133, filed on Oct. 8, 2021 (published as U.S. Pat. Pub. No. 2023-0112058), the entire contents of which is incorporated herein by reference in its entirety for all purposes.

BACKGROUND

A wide variety of surgical and medical assemblies and systems have been developed for surgical and medical uses. Some of these assemblies and systems include instruments used in spinal surgeries and the like. These assemblies and systems are manufactured by any one of a variety of different manufacturing methods and may be used according to any one of a variety of methods. Of the known medical assemblies, systems, and methods, each has certain advantages and disadvantages.

BRIEF SUMMARY

This disclosure provides design, material, manufacturing method, and use alternatives for surgical and medical devices, assemblies, and systems. There is an ongoing need to provide alternative surgical and medical devices, assemblies, and systems, as well as alternative methods for manufacturing and using surgical and medical devices, assemblies, and systems.

An example assembly includes a surgical bone drill bit having a distal end portion and a proximal end portion, a neuromonitoring connection in electrical communication with the surgical bone drill bit, and a shield extending over the distal end portion of the surgical bone drill bit. The shield may be configured to withdraw proximally relative to the distal end portion as the surgical bone drill bit is advanced into a subject's bone.

Alternatively or additionally to any of the embodiments in this section, the shield may be biased toward a distal end of the surgical bone drill bit.

Alternatively or additionally to any of the embodiments in this section, the shield may include teeth at a distal end of the shield.

Alternatively or additionally to any of the embodiments in this section, the assembly may further include a locking system in communication with the shield and the locking system may be biased to a shield lock position and is configured to be secured in a shield unlock position relative to the surgical bone drill bit.

Alternatively or additionally to any of the embodiments in this section, the locking system may further include an elongated member, a lock actuator configured to engage the elongated member and slide along the surgical bone drill bit, and one or more balls, and the lock actuator may have a lock position associated with the shield lock position and an unlock position associated with the shield unlock position and is configured to be secured in the unlock position.

Alternatively or additionally to any of the embodiments in this section, the surgical bone drill bit may have a lumen having one or more openings at an axial location along the lumen, the one or more openings being configured to receive the one or more balls.

Alternatively or additionally to any of the embodiments in this section, the assembly may be configured such that the elongated member moves along the lumen when the lock actuator is actuated from the lock position to the unlock position to allow the shield to withdraw proximally.

Alternatively or additionally to any of the embodiments in this section, when the lock actuator is at the lock position to prevent the shield from withdrawing proximally, the elongated member may extend within the lumen and positions the one or more balls within the one or more openings such that the one or more balls extend exterior of the surgical bone drill bit.

Alternatively or additionally to any of the embodiments in this section, the assembly may further include a proximal end of the shield includes a taper configured to drive the one or more balls into the one or more openings and the lumen as the shield withdraws proximally.

Alternatively or additionally to any of the embodiments in this section, the assembly may be configured such that inertia of the surgical bone drill bit rotating causes the lock actuator to transition from the unlock position to the lock position once drilling stops or the surgical bone drill bit is reversed.

Alternatively or additionally to any of the embodiments in this section, the assembly may further include a drill bit sleeve extending along at least a portion of the surgical bone drill bit and the drill bit sleeve and the shield may electrically insulate a conductive path extending from the neuromonitoring connection to a distal end of the surgical bone drill bit and the drill bit sleeve may be configured to receive a portion of the shield as the shield withdraws proximally.

Alternatively or additionally to any of the embodiments in this section, the surgical bone drill bit may be configured to rotate relative to the drill bit sleeve and the shield.

An example system includes a surgical bone drill bit having a distal end portion and a proximal end portion, a drill configured to receive the proximal end portion of the surgical bone drill bit, a neuromonitoring clip connected to a neuromonitoring connection on the surgical bone drill bit, a shield extending over the distal end portion of the surgical bone drill bit, and the shield may be configured to slide along the distal end portion of the surgical bone drill bit and the surgical bone drill bit is configured to rotate with respect to the shield.

Alternatively or additionally to any of the embodiments in this section, the system may further include a drill bit sleeve extending over the surgical bone drill bit at a location proximal to the shield and the drill bit sleeve may be configured to receive the shield as the shield slides along the distal end portion of the surgical bone drill bit.

Alternatively or additionally to any of the embodiments in this section, the drill bit sleeve may include a concave contoured portion configured receiving a user's grip and the surgical bone drill bit is configured to rotate with respect to the concave contoured portion of the drill bit sleeve.

Alternatively or additionally to any of the embodiments in this section, the system may further include a locking system in communication with the shield and the locking system may be biased to a lock position at which the shield is prevented from sliding along the distal end portion of the surgical bone drill bit and may be configured to be secured in an unlock position relative to the surgical bone drill bit at which the shield is able to slide along the distal end portion of the surgical bone drill bit.

Alternatively or additionally to any of the embodiments in this section, the system may further include a navigable surgical sleeve and the navigable surgical sleeve may define a lumen configured to receive the surgical bone drill bit and the shield extending over the distal end portion of the surgical bone drill bit.

An example method includes coupling a drill to a neuromonitoring bone drill bit, wherein an electrically insulating shield and an electrically insulating cover extend over the neuromonitoring bone drill bit, coupling a neuromonitoring clip to the neuromonitoring bone drill bit, securing a locking system in an unlocked position to allow the electrically insulating shield to withdraw proximally in response to engagement of the electrically insulating shield with tissue of a subject, advancing the neuromonitoring bone drill bit into bone of the subject, wherein advancing the neuromonitoring bone drill bit into tissue of the subject causes the electrically insulating shield extending over a distal end portion of the neuromonitoring bone drill bit to withdraw proximally relative to the distal end portion as the neuromonitoring bone drill bit advances into the tissue of the subject, and withdrawing the neuromonitoring bone drill bit from the tissue of the subject, wherein withdrawing the neuromonitoring bone drill bit from the tissue of the subject causes the electrically insulating shield to advance distally over the distal end portion of the neuromonitoring bone drill bit.

Alternatively or additionally to any of the embodiments in this section, the method may further include electrically stimulating the neuromonitoring bone drill bit with the neuromonitoring clip, and monitoring for a response to the stimulating indicative of a pedicle breach.

Alternatively or additionally to any of the embodiments in this section, the method may further include disposing the neuromonitoring bone drill bit in a guide tube held by a robotic arm, and the guide tube may constrain positioning of the neuromonitoring bone drill bit while the neuromonitoring bone drill bit is advanced into bone of the subject.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
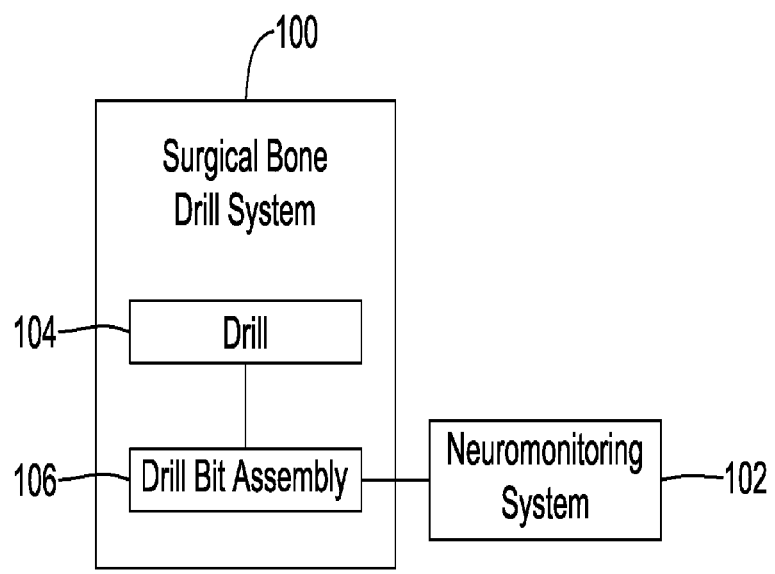
FIG. 1 is a schematic box diagram of an illustrative surgical bone drill system in communication with a neuromonitoring system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

Surgical bone drill systems may include a surgical bone drill bit configured to engage and drill holes into or through bone of a subject (e.g., a patient). In operation, the drill bit may be inserted to a surgical site through tissue of the subject and to the bone in which a hole is to be drilled. In some cases, the drill bit may be configured to provide an electrical stimulation to the tissue near the drill bit (e.g., the drill bit may be a neuromonitoring bone drill bit), where the electrical stimulation in or passing through the tissue may be sensed by a sensor or detector and the sensed measurements may be utilized for determining an integrity of the bone before, during, or after drilling the hole, monitoring for nerve location or damage, or other assessments and monitoring. When the bone in which a hole is being drilled is a pedicle of the vertebra, determining the integrity of the bone may be considered a "pedicle integrity assessment". Example systems, devices, and connections of systems and devices related to neuromonitoring are disclosed in: U.S. Pat. No. 7,657,308, filed Feb. 18, 2005, and titled SYSTEM AND METHODS FOR PERFORMING DYNAMIC PEDICLE INTEGRITY ASSESSMENTS; and U.S. Pat. No. 8,442,621, filed on Jun. 3, 2009, and titled SURGICAL TRAJECTORY MONITORING SYSTEM AND RELATED METHODS, which are hereby incorporated in their entirety for any and all purposes.

When inserting a neuromonitoring bone drill bit into the subject, an exposed cutting portion (e.g., a fluted portion) of the drill bit may physically contact tissue of the subject, which may inadvertently damage the tissue of the subject when the tissue is unintendedly contacted. Likewise, inadvertent or unwanted electrical connection between the drill bit and nearby tissue can cause errant neuromonitoring results. As such, protecting against undesired electrical or physical contact between the drill bit and tissue of the subject can be desirable. An illustrative neuromonitoring surgical bone drill bit assembly configured to block a cutting portion of a drill bit from unintended contact (e.g., physical contact, electrical contact, or both) between the drill bit and a subject's tissue may include a surgical bone drill bit having a neuromonitoring connection, and at least a portion of the drill bit may be covered by a retractable shield.

In the illustrative drill bit assembly, the neuromonitoring connection may be a conductive area in electrical communication with a cutting portion of the drill bit and configured to receive or otherwise attach to a neuromonitoring clip in communication with a neuromonitoring system for delivering electrical stimulation through the drill bit to a bone structure of the subject. The drill bit assembly may electrically insulate a conductive path from the neuromonitoring connection to a distal end of the cutting portion of the drill bit.

Part of the drill bit assembly configured to electrically insulate the conductive path may include the retractable shield. In some cases, the retractable shield may be distally-biased to cover a cutting portion of the drill bit. Further, the retractable shield may be configured to resist tissue from contacting the drill bit, where such contact may damage tissue or interfere with neuromonitoring results or bone or pedicle integrity assessments. When the cutting portion of the drill bit is driven into the bone of the subject, the shield may engage the bone as the drill bit advances into the bone such that the shield retracts relative to a distal end of the drill bit.

The shield may be locked or unlocked using a locking system. When locked, the shield may be prevented from retracting relative to the distal end of the drill bit. When unlocked, the shield may be biased toward the distal end of the drill bit and may be able to retract relative to the distal end of the drill bit.

In some cases, the locking system may include a lock actuator configured to be actuated to lock the shield in place or unlock the shield. In one example, the lock actuator may be adjusted from a lock position to an unlock position by moving the lock actuator in a proximal direction relative to the distal end of the drill bit. Proximally moving the lock actuator may result in withdrawing a lock mechanism (e.g., an elongated member, such as a pin, or other suitable lock mechanism) to permit movement of the shield. Although not required, the lock actuator may be secured in the unlock position by twisting or rotating the lock actuator after proximally withdrawing the shield actuator or by taking other action to secure the lock actuator in the unlock position. Further, although the locking system is described herein as including a lock actuator or other lock components that withdraw proximally to adjust from a lock position to an unlock position, it is contemplated that distal movement or other suitable movement may be utilized to adjust the lock actuator or other suitable components of the lock system from a lock position to an unlock position.

In some instances, the lock actuator may be automatically released from the unlock position. In one example, inertia or other forces of the surgical bone drill system may be utilized to automatically release the lock actuator from the unlock position. For example, inertia of the surgical bone drill system as drilling stops or as a drill bit rotational direction is reversed may cause the lock actuator to automatically release from the secured unlock position. Alternatively or additionally, the lock actuator may be released from the secured unlock position manually by reversing the steps used to secure the lack actuator in the unlock position or by taking other actions.

In one illustrative example of using the drill bit assembly configured to physically and electrically shield portions of the drill bit, the neuromonitoring drill bit may be utilized with a drill to form a neuromonitoring (e.g., an electromyography (EMG)) drill. Before or after connecting the drill bit assembly to the drill, the drill bit assembly may be inserted into a navigational sleeve that facilitates navigating to a desired surgical location.

To monitor a condition of a target bone or nerves around the target bone, a neuromonitoring clip in communication with a neuromonitoring system may be coupled to the drill bit assembly and the drill bit assembly may be inserted into a tool guide at a surgical site, where the tool guide may or may not be held by a surgical robot. As the drill bit is inserted into the subject at the surgical site (e.g., using navigational feedback), the lock actuator may be in a lock position and the shield may be biased toward and prevented from retracting relative to a distal end of the drill bit. Once the drill bit has been positioned adjacent a target bone of the subject, a surgeon or other medical professional may adjust the lock actuator to an unlock position and drill a pilot hole along a trajectory guided by the robot or a surgical navigation system. During drilling of the pilot hole, nerve health or pedicle integrity may be monitored using feedback in response to the electrical stimulation provided to the target bone by the drill bit.

As the drill bit passes into the bone of the subject, the shield may automatically retract or withdraw with respect to the distal end of the drill bit. For example, the user applies force to push the spinning drill bit into bone, but the distal end of the shield is unable to enter the bone as much as the drill bit. Consequently, as the drill bit enters the bone, the length of the drill assembly that remains outside of the bone decreases. To compensate for this decrease, the drill assembly outside of the bone reduces in length (e.g., because of a sliding relationship between two or more components). As the drill bit is withdrawn from the bone (e.g., once the pilot hole is sufficiently drilled or to clear debris from drill bit fluting), the shield moves toward the distal end of the drill bit in response to a bias force acting on the shield. As a result, the cutting portion of the drill bit is covered by the shield as the drill bit is backed out of the bone. In some cases, the lock actuator may automatically or manually return to the lock position once the drill bit stops rotating or reverses rotation. As the shield automatically extends distally over the drill bit, the surgeon may remove the drill from the surgical site and the tool guide without unintentionally contacting the cutting portion and the electrically conductive portion of the drill bit to the tissue of the subject.

Turning to the figures, FIG. 1 depicts a schematic box diagram of the surgical bone drill system 100 in communication with a neuromonitoring system 102 (e.g., an electromyography (EMG) system or other suitable neuromonitoring system). Although the neuromonitoring system 102 is depicted, other suitable electrical stimulation and monitoring systems may be utilized to monitor a health of tissue of a subject at or adjacent the surgical site. As depicted in FIG. 1, the drill system 100 may include a surgical bone drill 104 and a surgical bone drill bit assembly 106, where the drill bit assembly 106 may be inserted into and coupled to the drill 104 such that actuation of the drill 104 causes at least a portion of the drill bit assembly 106 to rotate.

The neuromonitoring system 102 may be in communication (e.g., electrical communication) with the drill bit assembly 106 or other portion of the surgical bone drill system 100 in electrical communication with a drill bit of the drill bit assembly 106. In some cases, the neuromonitoring system 102 may be mechanically, electrically, or mechanically and electrically coupled to the drill bit assembly 106, as discussed herein or otherwise.

The neuromonitoring system 102 may be any suitable neuromonitoring system configured to electrically stimulate tissue of a subject and monitor the electrical stimulation. As discussed, in some cases, the neuromonitoring system 102 may be an EMG system. Although other systems are contemplated, example EMG systems and bone integrity assessments are disclosed in U.S. Patent Application Publication No. US 2005/0004623, filed on Oct. 30, 2002, and titled SYSTEM AND METHODS FOR PERFORMING PERCU- TANEOUS PEDICLE INTEGRITY ASSESSMENTS, which is hereby incorporated by reference in its entirety for any and all purposes.

Application of the electrical stimulation (e.g., electrical signals or other suitable electrical stimulation) may be accomplished in any suitable manner including, but not limited to, applying voltage or current pulses of varying magnitude or frequency to the drill bit assembly 106. Further, the neuromonitoring system 102 may monitor the electrical stimulation through the subject's body directly or indirectly (e.g., through detecting muscle activity or otherwise indirectly detecting) with a detector to assess an integrity of a bone in which the drill bit assembly 106 is being used to drill a hole and determine whether any nerves adjacent the bone may be innervating as a result of applying the stimulation signal to the drill bit assembly 106. In one example, the neuromonitoring system 102 may use evoked muscle action potential (EMAP) monitoring techniques, where EMG responses of muscle groups associated with identified nerves are measured. Alternatively or additionally, the subject's response to the electrical stimulation may be visually monitored.

Figure 2:
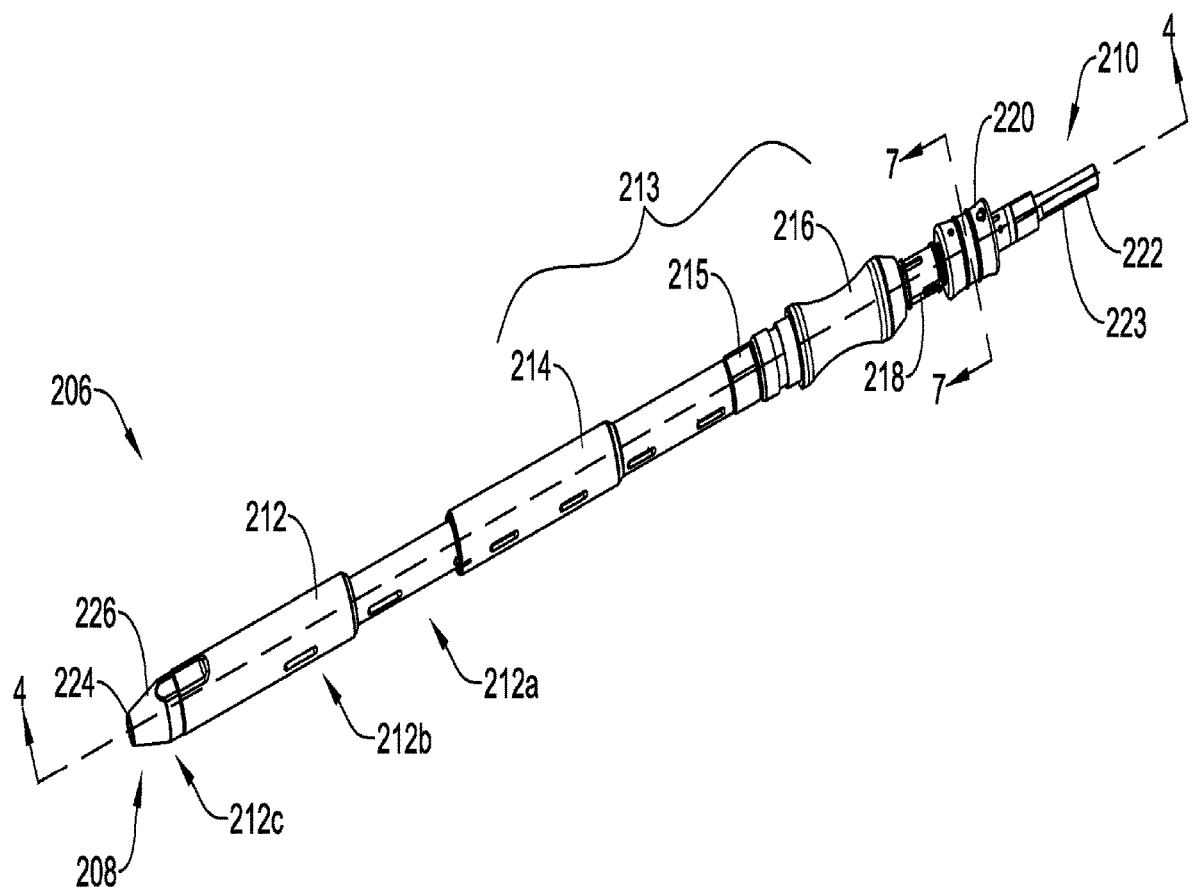
FIG. 2 is a schematic perspective view of an illustrative surgical bone drill bit assembly.

FIG. 2 is a schematic perspective view of an illustrative configuration of a surgical bone drill bit assembly 206 having a distal end portion 208 and a proximal end 210. Among other components, the drill bit assembly 206 may include a shield 212, a drill bit sleeve 213, a neuromonitoring connection portion 218, a lock actuator 220, and a drill bit shank 222 of a surgical bone drill bit 223. In some cases, the shield 212 in combination with the sleeve 213 or other components of the drill bit assembly 206 may be configured to electrically insulate a conductive path extending from the neuromonitoring connection portion 218 to a distal end of the surgical drill bit 223.

In some cases, the sleeve 213 may be configured to extend over a drill bit of the drill bit assembly 206 and may include a cover 214, a spacer 215, a contoured portion 216, other suitable components, or combinations thereof. The sleeve 213 may be formed as a single component or may be multiple components longitudinally extending along a drill bit of the drill bit assembly 206. As depicted in FIG. 2, the sleeve 213 may include the cover 214, the spacer 215, and the countered portion 216.

In some cases, the shield 212 and the cover 214 may be configured to enter a surgical site inside of a subject during use of the drill bit assembly 206 with a drill (e.g., the drill 104 or other suitable drill). Further, the contoured portion 216, the neuromonitoring connection 218, the lock actuator 220, and the drill bit shank 222 may be configured to remain proximal of the surgical site, outside of the subject, but this is not required. Other configurations of the components of the drill bit assembly 206 are contemplated Turning to individual components of the drill bit assembly 206 depicted in FIG. 2, the drill bit shank 222 may be located at the proximal end 210 of the drill bit assembly 206 and may be configured to be inserted into and engaged by a drill. Although not required, the drill bit shank 222 may have a male keyed configuration that is intended to be received in a female keyed configuration of a drill. In some cases, the drill bit shank 222 may be part of the drill bit 223, but this is not required and the drill bit shank 222 may be one or more components separate from and in rotatable communication with the drill bit 223, such that when a drill engaging the drill bit shank 222 causes rotation of the drill bit shank 222, the drill bit 223 also rotates.

The lock actuator 220 may have any suitable configuration or location along the drill bit assembly 206 that facilitates a user locking or unlocking the shield 212 in response to movement of the lock actuator 220. In one example, the lock actuator 220 may be located proximal of the shield 212, but this is not required.

The neuromonitoring connection portion 218 may be located at any suitable location along the drill bit assembly 206 such that the neuromonitoring connection portion 218 may be in electrical communication with a drill bit of the drill bit assembly 206 and configured to facilitate an electrical connection between an electrical stimulation and monitoring system (e.g., the neuromonitoring system 102 or other suitable neuromonitoring system) and the drill bit assembly 206. In some cases, the neuromonitoring connection portion 218 may be a conductive area that is configured to attach to a neuromonitoring clip mechanically and electrically coupling the drill bit assembly 206 to the neuromonitoring system or other electrical stimulation and monitoring system. Although not required, the neuromonitoring clip connection portion 218 may be in contact (e.g., electrical contact, physical contact, or both) with the drill bit 223 and may rotate with the drill bit 223 relative to the coupled neuromonitoring clip.

The contoured portion 216 or grip portion of the sleeve 213 may be located any suitable location along the drill bit assembly 206 such that a user (e.g., a surgeon or other medical provider in a procedure room) may grasp the contoured portion 216 between at least two digits of their hand during use of the drill bit assembly 206. The contoured portion 216 may have one or more contoured portions configured for receiving a user's grip. For example, the contoured portion 216 of the drill bit assembly 206 may have a longitudinal and circumferential concave profile, as depicted in FIG. 2, two longitudinally concave profiles circumferentially spaced from one another on opposing radial sides of the drill bit assembly 206, two or more longitudinally concave profiles circumferentially spaced unequal distances from one another, indents, protrusions or both that are configured to facilitate gripping the contoured portions, other suitable profiles that facilitate gripping the drill bit assembly 206, or combinations thereof. In one example use of the contoured portion 216, a user may hold the drill connected to the drill bit assembly 206 with a first hand and grip the contoured portion 216 with two digits (e.g., between a thumb and an index finger, or other set of digits) with a second hand to stabilize the drill bit 223 at a target location while the drill bit 223 rotates with respect to the contoured portion 216.

The cover 214 of the sleeve 213 may be located at least partially distally of the neuromonitoring connection 218 and may be comprised of one or more components along the drill bit assembly 206 to at least partially electrically insulate a conductive path of the drill bit assembly 206 between the neuromonitoring connection 218 and a distal end of the drill bit. In some cases, the cover 214 may be located proximal of the shield 212. Although not required, the cover 214 may be configured to receive at least a portion of the shield 212 or otherwise facilitate movement or sliding of the shield 212 in responses to forces acting on the shield 212.

The shield 212 may be located at the distal end portion 208 of the drill bit assembly 206 and may extend proximally therefrom so as to cover a distal end of the drill bit 223 of the drill bit assembly 206. As discussed, the shield 212 may be configured to retract or withdraw by sliding or moving proximally along or with respect to a distal end portion of a drill bit of the drill bit assembly 206 as the drill bit is advanced into a subject's bone or other tissue and then automatically extend distally as the drill bit is withdrawn from the subject's bone or other tissue to cover a portion of the drill bit that had been inserted into the subject's bone or other tissue. As the shield 212 retracts or withdraws along a distal end of the drill bit 223, the sleeve 213 (e.g., the cover 214 or other portion of the sleeve 213) may receive the shield 212.

The shield 212 may have any suitable configuration that facilitates longitudinally moving or sliding (e.g., withdrawing or retracting and extending) the shield 212 along the drill bit 223 of the drill bit assembly 206. In one example configuration of the shield 212, the shield 212 may have a first portion 212*a* (e.g., a reduced diameter portion or other portion), a second portion 212*b* (e.g., an expanded diameter portion), and a third portion 212*c* (e.g., a tip portion), but the shield 212 is not required to have three portions. When included, the first portion 212*a* may be configured to be received within an inner diameter of the cover 214 as the shield 212 withdraws proximally and the second portion 212*b* may form or act as a shoulder relative to the first portion 212*a* such that a proximal end of the second portion 212*b* may engage a distal end of the cover 214 to limit a proximal withdrawal or retraction of the shield 212. Other suitable configurations, of the inner diameter of the cover 214, the outer diameter of the first portion 212*a* of the shield 212, and the outer diameter of the second portion 212*b* of the shield 212 are contemplated.

The third portion 212*c* of the shield 212 may form a distal end of the shield 212 and terminate at a terminal tip 224. Though not required, the third portion 212*c* may have a tapering portion 226 that terminates at or prior to the terminal tip 224, where the tapering portion 226 may facilitate inserting the drill bit assembly 206 to a target bone at a surgical site by guiding obstructions contacting the tapering portion 226 away from the drill bit assembly 206. In some cases, the terminal tip 224 of the shield 212 may be flat (e.g., is in a plane that is perpendicular or is otherwise transverse to a longitudinal access of the drill bit assembly 206), as depicted in FIG. 2, curved, a rigid terminal tip, a soft or pliable terminal tip for engaging the target bone, a serrated or toothed terminal tip for engaging the target bone, one or more other configurations, or combinations thereof. Further, in some cases, the third portion 212*c* may be separable from or releasably engageable with one or more other portions of the shield 212.

Figure 3:
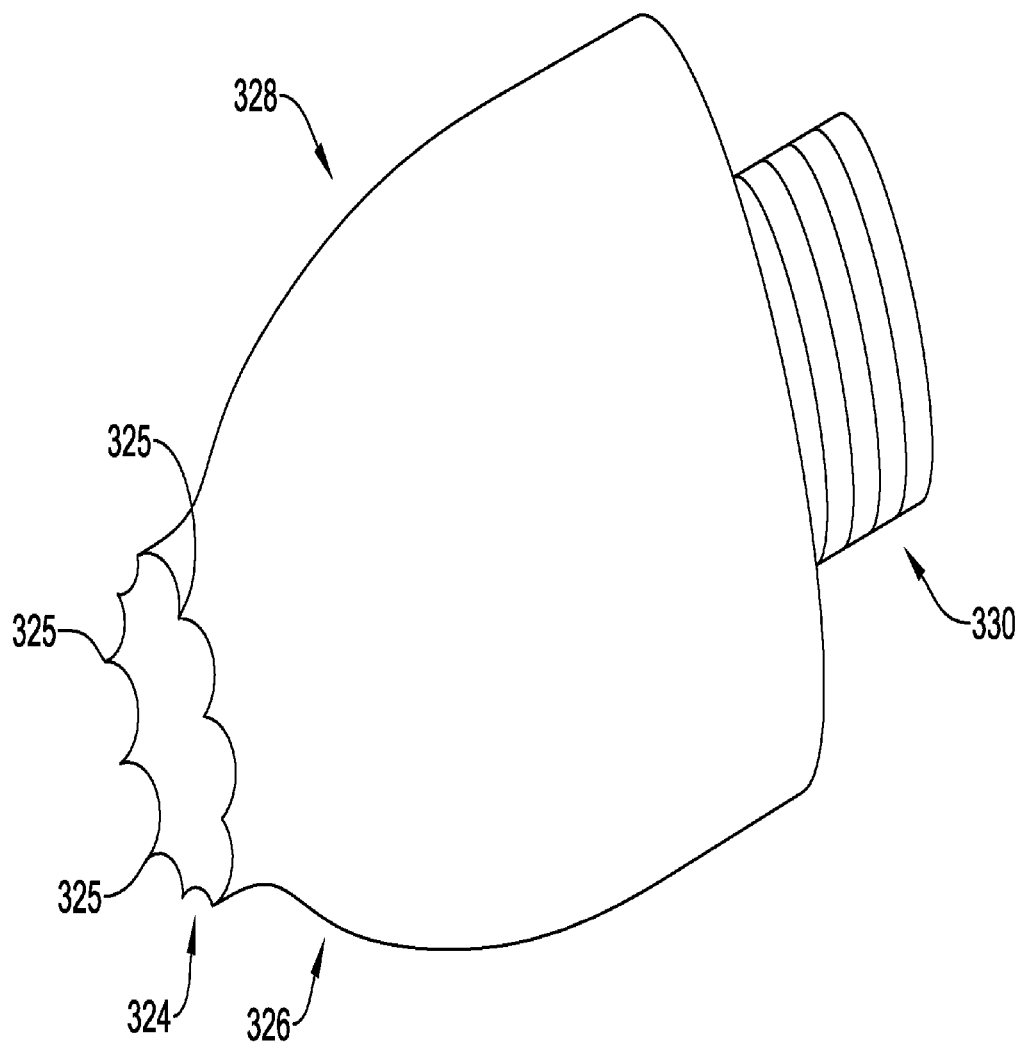
FIG. 3 is a schematic perspective view of an illustrative tip for a shield of a surgical bone drill bit.

FIG. 3 depicts a schematic perspective view of an illustrative configuration of a distal end component 328 for the shield 212, where the distal end component 328 may have a terminal tip 324 with a serrated or toothed configuration. In some cases, the distal end component 328 may form, or at least form part of, the third portion 212*c* of the shield 212, which was discussed above with respect to FIG. 2.

As depicted in FIG. 3, the distal end component 328 may include a tapering portion 326 that extends distally to an extension (e.g., a portion of the distal end component 328 extending from a distal end of the taper portion 326 to the terminal tip 324) forming a serrated or toothed terminal tip 324. Although the extension forming the serrated or toothed terminal tip 324 is depicted as relatively short compared to an entire length between a proximal terminal end of the distal end component 328 and the terminal tip 324, the extension may be further elongated (e.g., longer) or may be shorter than an entire length of the extension depicted in FIG. 3. Further, although the extension forming the terminal tip 324 is depicted as being a reduced diameter relative to a proximal portion of the distal end component 328 extending proximally of the taper portion 326, the extension may have a same diameter as or a larger diameter than the proximal portion of the distal end component 328.

The serrated or toothed terminal tip 324 may take on any suitable configuration that facilitates stabilizing the drill bit assembly 206 as the assembly is brought into contact with a target bone or other tissue and as a drill bit of the drill bit assembly 206 drills into the target bone or other tissue. As depicted in FIG. 3, the terminal tip 324 may include a plurality of teeth 325 (for clarity purposes, not all teeth are labeled) circumferentially spaced around the terminal tip 324 such that the teeth are configured to engage bone or other tissue, but other serrated or toothed configurations are contemplated.

Although the distal end component 328 for the shield 212 may be monolithically or integrally formed with other portions or components (e.g., the first portion 212*a*, the second portion 212*b*, etc.) of the shield 212, the distal end component 328 may be configured to be releasably engaged with a portion of the shield 212 without destroying the shield 212 or otherwise preventing the shield 212 from being used. In some cases, the distal end component 328 may include a connector portion 330 configured to engage a portion (e.g., a distal end of the second portion 212*b* or other suitable portion) of the shield 212 to form at least part of the third portion 212*c* and facilitate removal from the engaged portion of the shield 212. Although the connector portion 330 is depicted as a threaded male connector, the connector portion 330 may be configured to connect with another portion of the shield 212 in one or more other manners including, but not limited to, through female-male connection, a snap connection, a friction fit connection, a ball detent connection, a luer lock connection, or other suitable connections. Further, in some cases, the distal end component 328 may be configured to be permanently connected (e.g., connected through an adhesive connection or other suitable fixed connection) to a portion of the shield 212, such that the distal end component 328 cannot be removed or separated from the portion of the shield 212 without causing destruction of the shield 212.

Figure 4:
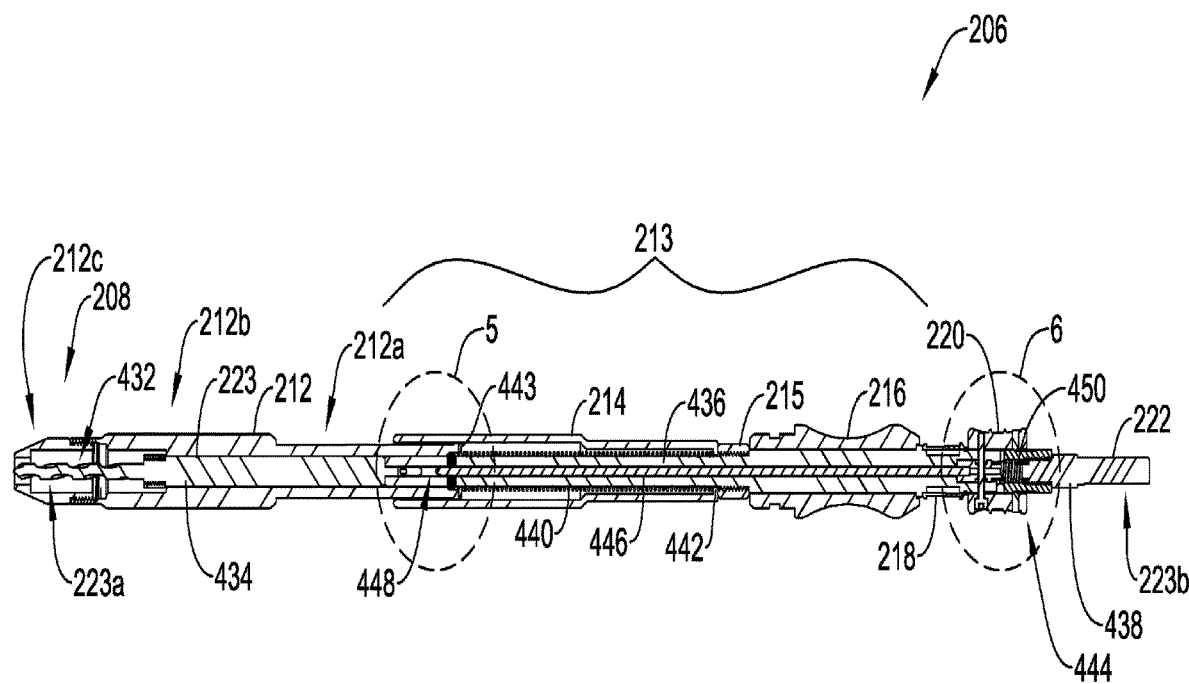
FIG. 4 is a schematic cross-sectional view of the illustrative bone drill bit assembly of FIG. 2, taken along line 4-4.

FIG. 4 depicts a schematic cross-sectional view of the drill bit assembly 206, taken along line 4-4 in FIG. 2. As depicted in FIG. 4, the surgical bone drill bit 223 may extend along a length of the drill bit assembly 206 and may be covered by one or more components of the drill bit assembly 206. Further, the drill bit assembly 206 may include a locking system 444 in communication with the shield 212, where the locking system 444 may extend at least partially through the drill bit 223.

The drill bit 223 may have a distal end portion 223*a* and a proximal end portion 223*b*. A cutting portion 432 (e.g., a fluted portion or other cutting portion) of the drill bit 223 may be located at the distal end portion 223*a* and the drill bit shank 222 may be located at the proximal end portion 223*b*.

The drill bit 223 may be formed from any suitable number of components. For example, the drill bit 223 may be monolithically formed from a single component or formed from two or more components. When formed from two or more components, the components may be connected to each other with one or more connection techniques configured to withstand high rotational speeds typical of surgical bone drills including, but not limited to, welded connections, adhesive connections, threaded connection, other suitable connections, or combinations of connections. As depicted in FIG. 4, the drill bit 223 may be formed from a solid first component 434 defining the cutting portion 432, a second component 436 being hollow or having a lumen 448 extending at least partially therethrough that may be welded to the first component 434, and a third component 438 forming the drill bit shank 222 and connected to the second component 436 via a threaded connection.

As depicted in FIG. 4, one or more components of the drill bit assembly 206 may extend over or cover the drill bit 223. In some cases, the one or more components of the drill bit assembly 206 extending over or covering the drill bit 223 may be configured to electrically insulate the drill bit 223 or prevent unintended exposure of the cutting portion 432 of the drill bit 223 to bone or tissue of a subject on which the drill bit assembly is to be or is being used. In one example, the shield 212 and the sleeve 213 (e.g., the cover 214, the spacer 215, and the contoured portion 216) may be configured to electrically insulate a conductive path extending through the drill bit 223 (e.g., a conductive path extending from the neuromonitoring connection portion 218 to the distal end or tip of the drill bit 223 or other suitable conductive path).

The shield 212 and the sleeve 213 may be configured from any suitable material configured to electrically insulate a conductive path through the drill bit 223. In some cases, the shield 212 may be made out of one or more same materials as or one or more different materials than one or more materials of the components of the sleeve 213. In one example, the shield 212 may be formed from a rigid electrically insulating material that facilitates contacting a subject's bone or tissue and the contoured portion 216 of the sleeve 213 may be formed from a resilient electrically insulating material that facilitates a user gripping the contoured portion. Other configurations are contemplated.

Any suitable rigid, flexible, or resilient biocompatible, electrically insulating material may be utilized for the components of the shield 212 and the sleeve 213. Example electrically insulating materials may include, but are not limited to, ceramics, natural polymers, synthetic polymers, cellulose, silk, shellac, gelatin, silicone, polyphenylsulfone (PPSU), homopolymer polypropylene (PP), polyvinyl alcohol (PVA), polydimethylsiloxane (PDMS), polylactide (PLA), polycaprolactone (PCL), polycaprolactone (PCL), polyglycerol-co-sebacate (PGS), polylactic-co-glycolic acid (PLGA), acrylics, or other suitable insulating materials.

As depicted in FIG. 4, the drill bit assembly 206 may include a first spring 440 that may be configured to bias the shield 212 toward the distal end portion 223a of the drill bit 223. In some cases, the shield 212 may be biased to cover the cutting portion 432 of the drill bit 223 or other portions of the drill bit 223. In one example configuration, the first spring 440 may be configured to engage an interior ledge 442 of the cover 214 and a proximal end of the shield 212 (e.g., a proximal cap 443 or other suitable portion of the shield 212), as depicted in FIG. 4. However, other suitable configurations of the first spring 440 relative to the shield 212 are contemplated. Further, biasing mechanisms in addition to or as alternatives to the first spring 440 may be utilized.

The locking system 444 may be in communication with the shield 212 and may be configured to adjust between a shield lock position at which the shield 212 is prevented from withdrawing or retracting with respect to the distal end portion 223a of the drill bit 223 and a shield unlock position at which the shield 212 is able to withdraw or retract with respect to the distal end portion 223a of the drill bit 223. Among other components, the locking system 444 may include an elongated member 446 extending along the drill bit 223 (e.g., the elongated member 446 may extend through the lumen 448 of the drill bit 223) and the lock actuator 220 may be configured to engage the elongated member 446 and slide along the surgical drill bit 223 to adjust the locking system 444 between the shield lock position and the shield unlock position. In some cases, the locking system 444 may be biased to the shield lock position by a second spring 450 or other suitable biasing mechanism.

Figure 5:
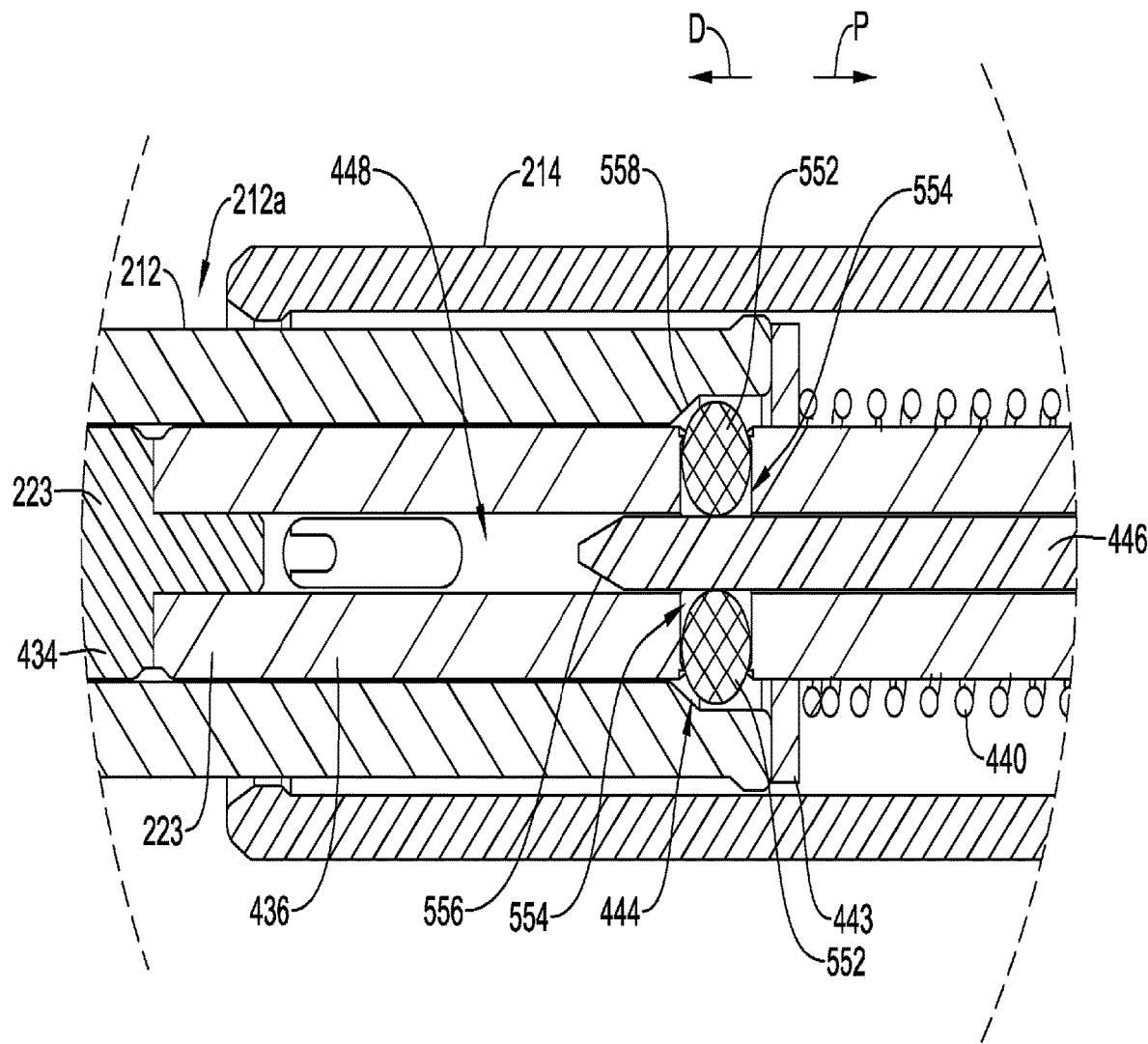
FIG. 5 is a schematic enlarged view of the area within circle-5 in FIG. 4.
Figure 6:
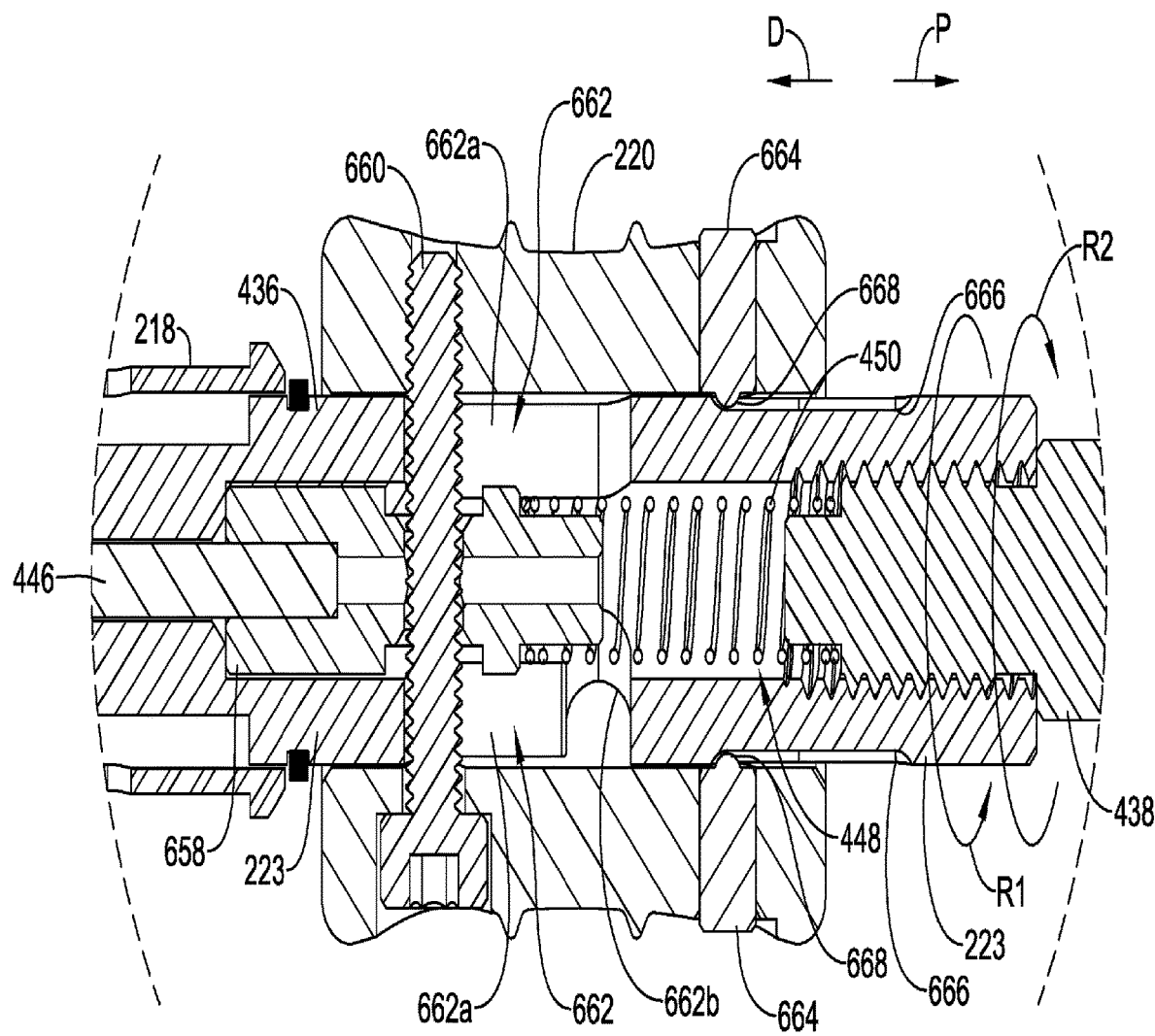
FIG. 6 is a schematic enlarged view of the area within circle-6 in FIG. 4.

An illustrative configuration of the locking system 444 is more fully described with respect to FIGS. 5 and 6. FIG. 5 is an enlargement of the drill bit assembly 206 within circle-5 in FIG. 4. FIG. 6 is an enlargement of the drill bit assembly 206 within circle-6 in FIG. 4.

In addition to the lock actuator 220 and the elongated member 446, the locking system 444 may include one or more balls 552 (e.g., the locking system 444 may include two balls, as depicted in FIG. 5, but one, three, or other suitable number of balls 552 may be utilized) or other suitable adjustable components configured to engage the shield 212 and prevent the shield 212 from retracting or withdrawing along the drill bit 223 when the elongated member 446 is distally positioned. In some cases, the one or more balls 552 may be configured to be positioned in or received by one or more openings 554 in the drill bit 223, the lumen 448 in the drill bit 223, or both.

The one or more openings 554 may extend outward (e.g., radially outward or otherwise extend outward) from one or more axial locations along a central axis of the drill bit 223. Further, the one or more openings 554 may extend from the lumen 448 through an exterior surface of the drill bit 223, but other configurations of the openings 554 are contemplated. Although the openings 554 are depicted as extending radially outward from the lumen 448 in a central plane that is perpendicular to a central axis of the lumen 448, the openings 554 may be in one or more planes intersecting the central axis of the lumen 448 at one or more other angles.

In operation, when the locking system 444 is in the shield lock position, as depicted in FIG. 5, the elongated member 446 may extend through the lumen 448 and may be biased in a distal direction D such that the elongated member 446 may extend distally to or beyond the openings 554 in or through the drill bit 223. In some cases, as the elongated member 446 reaches or passes through an axial location of the balls 552, a tapered portion 556 of the elongated member 446 may engage the one or more balls 552 and urge the one or more balls 552 into the openings 554. Further, the elongated member 446 may maintain the balls 552 in or extending through the openings 554 while the locking system 444 is in the shield lock position. When the balls 552 are maintained within the openings 554 of the drill bit 223, the balls 552 may extend at least partially through an outer perimeter of the openings 554 and engage the shield 212 as it attempts to retract or withdraw along the drill bit assembly 206. Even if a bias force of the first spring 440 is overcome by a force acting on the shield 212 in a proximal direction P, the locking system 444 prevents proximal movement of the shield 212 when the locking system 444 is in the shield lock position.

As described in further detail below, when the locking system 444 is in the shield unlock position, the elongated member 446 may withdraw in the proximal direction P, which may allow the one or more balls 552 to move freely (e.g., without obstruction from the elongated member 446) within the openings 554, the lumen 448, or both. As such, when a force acting on the shield 212 in the proximal direction P overcomes the bias force of the first spring 440 in the distal direction D, the shield 212 may engage the one or more balls 552 to the extent the balls 552 are extending beyond an outer perimeter of the drill bit 223, direct the one or more balls 552 into the openings 554, and withdraw or retract with respect to the distal end portion 223a of the drill bit 223. In some cases, an interior circumference of the shield may have a tapered portion 558 that is configured to engage the one or more balls 552 and direct the one or more balls 552 into the openings 554 and the lumen 448.

Although the elongated member 446 is depicted in the Figures as being configured to withdraw in the proximal direction P when the locking system 444 is adjusted from the shield lock position to the shield unlock position, this is not required. In some cases, the locking system 444 may be configured such that the elongated member 446 or other components of the locking system 444 may move in the distal direction D in response to the locking system 444 being adjusted from the shield lock position to the shield unlock position. That is, the elongated member 446 or other suitable components of the locking system 444 may be configured to translate axially (e.g., in a proximal or a distal direction) to facilitate adjusting the locking system 44 from the shield lock position to the shield unlock position.

In the locking system 444 described with respect to FIG. 5, a sum of the diameters of the two balls 552 and the diameter of the elongated member 446 may be a value that is greater than an outer diameter of the drill bit 223 at the axial location of the openings 554 such that the balls 552 extend through the openings 554 and engage the shield 212 to prevent movement of the shield 212 in the proximal direction P when the locking system 444 is in the shield lock position. Further, a sum of the diameter of the two balls 552 may be a value that is less than the outer diameter of the drill bit 223 at the axial location of the openings 554 such that the balls 552 may slide into the openings 554, the lumen 448, or both as the shield moves in the proximal direction P when the locking system 444 is in the shield unlock position. In some cases, a diameter of one of the one or more balls 552 may be greater than the diameter of the lumen 448 so as to prevent the ball 552 from traveling longitudinally through the lumen 448. However, other configurations are contemplated and diameters may be dependent on a number of balls 552 used, openings 554 used, or other suitable factors.

As discussed, the locking system 444 may be adjustable between the shield lock position and the shield unlock position by manipulating the lock actuator 220. FIG. 6 depicts a schematic cross-sectional view of the lock actuator 220 and a connection between the lock actuator 220 and the elongated member 446.

The lock actuator 220 and the elongated member 446 may be connected in any suitable manner. In some cases, the lock actuator 220 and the elongated member 446 may be directly connected to one another through one or more connection techniques. For example, the elongated member 446 can cooperate with the lock actuator 220 such that a user can manipulate the elongated member 446 (e.g., via proximal or distal movement) to switch the locking system 444 between the shield lock position and the shield unlock position. In other cases, the lock actuator 220 and the elongated member 446 may be connected to one another indirectly via a connector component 658, as depicted in FIG. 6, and one or more coupling or connection techniques.

When included, the connector component 658 may be located within or about the drill bit 223. The connector component 658 may be configured to slide or otherwise move in the distal direction D and the proximal direction P with the elongated member 446 and the lock actuator 220 and relative to the drill bit 223, as the lock actuator 220 is adjusted to switch the locking system 444 between the shield lock position and the shield unlock position.

The one or more connection techniques for connecting the elongated member 446, the connector component 658 (when included), and the lock actuator 220 may include any suitable techniques for connecting rotational components of a medical or surgical device to one another. Example suitable connection types include, but are not limited to, adhesive connections, weld connections, screw or bolt connections, threaded connections, luer lock connections, friction fit connections, crim connections, swag connections, brazed connections, other types of connections, or combinations thereof. In the example depicted in FIG. 6, the connector component 658 may receive a portion of the elongated member 446 and may be connected to the elongated member 446 via a weld connection or an adhesive connection. Further, in the example, the connector component 658 may be connected to the lock actuator 220 via a screw connection or other suitable connection in which a connector 660 (e.g., a pin, a screw, or other suitable connector) may engage the lock actuator 220 (e.g., threads of the lock actuator 220 or other features of the lock actuator 220) and extend through an opening of the drill bit 223 and an opening of the connector component 658.

To facilitate the movement of the lock actuator 220, the drill bit 223 may include one or more openings 662 extending from an exterior circumference of the drill bit 223 to the lumen 448 and may be configured to receive the connector 660 securing the lock actuator 220 to the drill bit 223 and the connector component 658. The openings 662 in the drill bit 223 may take on any suitable configuration. In some cases, the openings 662 may be configured to facilitate receiving the connector 660 or other feature securing the lock actuator 220 to the other components of the drill bit assembly 206 and facilitating adjustment of the lock actuator 220 between a shield lock position and an unlock position.

In some cases, the openings 662 may include an axial portion 662a (e.g., an elongated axial portion that extends at least partially in an axial direction) and a circumferential portion 662b (e.g., a circumferential portion that extends at least partially in a circumferential direction) in communication with the axial portion 662a. The circumferential portion 662b may extend from the axial portion 662a at any suitable location along the axial portion 662a. In one example, the circumferential portion 662b may extend from a proximal end of the axial portion 662a, as depicted in FIG. 6, to facilitate securing the locking system 444 in the shield unlock position relative to the drill bit 223.

The axial portion 662a may extend in an axial direction any suitable distance required to adjust the locking system 444 between the shield lock position and the shield unlock position. The circumferential portion 662b may extend circumferentially any suitable distance around the drill bit 223 to facilitate securing the locking system 444 in the shield unlock position or providing feedback to a user indicating the locking system 444 is in the shield unlock position.

Figure 7:
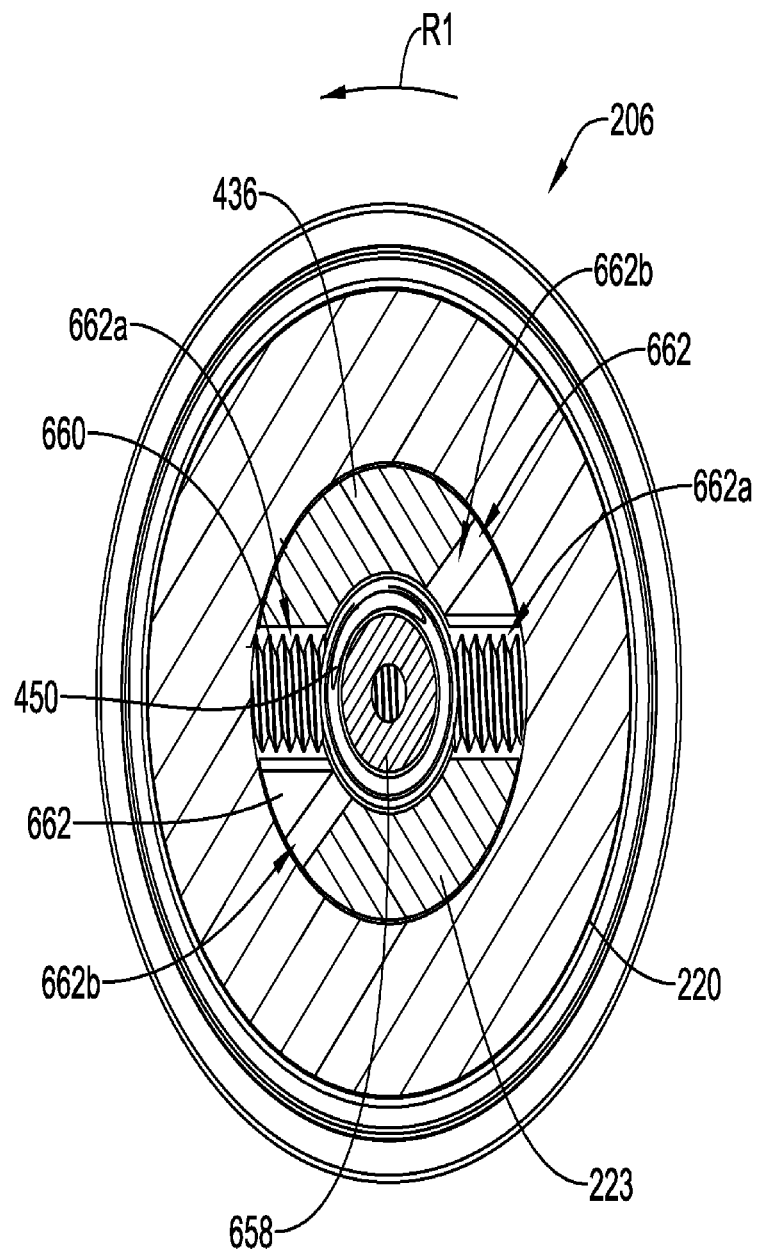
FIG. 7 is a schematic cross-sectional view of the illustrative bone drill bit assembly of FIG. 2, taken along line 7-7.

The axial portion 662a and the circumferential portion 662b of the openings 662 are further depicted in FIG. 7, which is a schematic cross-sectional view taken long line 7-7 in FIG. 6. As depicted in FIG. 7, the connector 660 may be located in the axial portion 662a of the openings 662 while the lock actuator 220 is in the lock position. To secure the lock actuator 220 in the unlock position, the lock actuator may be manually adjusted against a bias force of the second spring 450 in a proximal direction (e.g., out of the page, toward a reader of FIG. 7) relative to the drill bit 223 until the connector 660 reaches an axial location of the circumferential portion 662b of the openings 662. Once the connector 660 has reached the axial location of the circumferential portion 662b, the lock actuator 220 may be rotated in a rotational direction R1 relative to the drill bit 223 such that the connector 660 is within the circumferential portion 662b of the openings 662 and the bias force of the second spring 450 seats the connector 660 in the circumferential portion 662b.

Although not depicted, the circumferential portion 662b of the openings 662 may include an indent or further slot circumferentially spaced from the axial portion 662a. Such an indent or further slot may be configured to receive the connector 660 so as to secure the connector 660 in the unlocked configuration.

Returning to FIG. 6, an operation of the locking system 444 is discussed. The depicted locking system 444 is in a shield lock position with the lock actuator 220 in a lock position, such that the elongated member 446 may extend through the lumen 448 of the drill bit 223 and position the balls 552 within and at least partially through the openings 554 to prevent the shield 212 from withdrawing in the proximal direction relative to the distal end portion 223a of the drill bit 223 (e.g., as shown in FIG. 5). The second spring 450 (e.g., extending in the lumen 448 of the drill bit 223 and acting on the connector component 658 and the third component 438 of the drill bit 223 or otherwise acting on the lock actuator 220) or other bias mechanism may bias the lock actuator 220 to the lock position and the locking system 444 to the shield lock position.

To adjust the lock actuator 220 to the unlock position and thus, the locking system 444 to the shield unlock position, the lock actuator 220 may be adjusted against the force of the second spring 450 in the proximal direction P relative to the drill bit 223, such that the connector 660 may slide or otherwise move in the proximal direction P relative to the drill bit 223 within the axial portion 662a of the openings 662. As the lock actuator 220 is adjusted in the proximal direction P relative to the drill bit 223, the elongated member 446 may move in the proximal direction P relative to the drill bit 223 such that balls may enter the openings 554 and the lumen 448 to allow the shield 212 to withdraw proximally relative to the drill bit 223 in response to forces acting on the shield 212 in the proximal direction P.

Once the lock actuator 220 is in the unlock position and thus, the locking system 444 is in the shield unlock position, the locking system 444 may be secured in the shield unlock position. For example, once the lock actuator 220 is in the unlock position, the lock actuator 220 may be rotated in the rotational direction R1 relative to the drill bit 223 such that the connector 660 may slide in the circumferential portion 662b of the openings 662 to secure the lock actuator 220 in the unlock position and secure the locking system 444 in the shield unlock position, as discussed above. When the connector 660 is positioned in the circumferential portion 662b of the openings 662, the bias force of the second spring 450 may be prevented from causing the lock actuator 220 to return to its lock position without additional forces acting on the lock actuator 220 that facilitate returning to the lock position.

The lock actuator 220 may be manually or automatically adjusted from the secured unlock position to the lock position. To return the lock actuator 220 to the lock position from the secured unlock position, the lock actuator 220 may be manually rotated in a rotational direction R2 relative to the drill bit 223, which may be opposite or substantially opposite the rotational direction R1. Such rotation of the lock actuator 220 may cause the connector 660 to move within the circumferential portion 662b of the openings 662 to the axial portion 662a, where the lock actuator 220 may be released from a secured position and the bias force of the second spring 450 may cause the connector 660 to move within the axial portion 662a of the openings 662. As a result, the lock actuator 220 may return to the lock position and thus, the locking system 444 may return to the shield lock position.

Alternatively or additionally to manually returning the lock actuator 220 to the lock position, the lock actuator 220 may be configured to automatically adjust from the secured unlock position to the lock position in response to an adjustment in inertia in, rotation of, or torque on the drill bit 223. For example, if the drill bit 223 stops rotating in a first direction (e.g., the rotational direction R1) or if the drill bit 223 starts rotating in a second direction (e.g., the rotational direction R2) opposite or substantially opposite the first direction, an inertia of the drill bit 223 or an associated change in torque of the drill bit assembly 206 may cause the lock actuator 220 to rotate in the rotational direction R2 relative to the drill bit 223 and with the bias force of the second spring 450, automatically return to the lock position. Other configurations for manually or automatically switching the locking system 444 from the shield unlock position to the shield lock position are contemplated.

Further, the lock actuator 220 may include one or more first guide components 664 configured to engage or couple with one or more second guide components 666 on the drill bit 223, where the engagement or coupling is configured to facilitate longitudinally, rotationally, or longitudinally and rotationally translating the lock actuator 220 relative to the drill bit 223. In one example configuration depicted in FIG. 6, the lock actuator 220 may include one or more first guide components 664 which may have a protrusion 668 configured to engage or couple with an indentation of the second guide component 66 in the drill bit 223. In another example, the first guide components 664 of the lock actuator 220 may include an indentation and the second guide components 666 of the drill bit 223 may include a protrusion configured to engage the indentation of the first guide components 664. Other designs and configurations of the first guide component 664 and the second guide component 666 are contemplated.

Although the first spring 440, the second spring 450, force directions applied by the first spring 440 and the second spring 450, and directions of movement of components of the locking system 444 are discussed with respect to the configuration of components of the locking system 444 depicted in FIGS. 4-7, it is contemplated that the locking system 444 may take on one or more other suitable configurations. For example, there may be additional or alternative biasing mechanisms configured to apply forces to components of the locking system 444 and the drill bit assembly 206 in one or more other suitable manners.

The drill bit assembly 206 described herein may include components configured to rotate with the drill bit 223 and components not configured to rotate with the drill bit 223 (e.g., the drill bit 223 may be configured to rotate relative to these components). In some cases, the neuromonitoring connection 218 and the locking system 444 (e.g. the lock actuator 220, the first spring 440, the elongated member 446, the second spring 450, the balls 552, the connector component 658, the connector 660, or other components of the locking system 444), or other suitable components of the drill bit assembly 206 may be configured to rotate with the drill bit 223. Further, the shield 212, the sleeve 213 (e.g., cover 214, the spacer 215, the contoured portion 216, or other suitable components of the sleeve), or other suitable components of the drill bit assembly 206 may be configured such that the drill bit 223 rotates relative to these components. Such a configuration may result in the components of the drill bit assembly 206 that are exposed to a subject's tissue at a surgical site, other than the drill bit 223, not rotating with the drill bit 223 so as to mitigate an injury risk to the patient at the surgical site.

Figure 8:
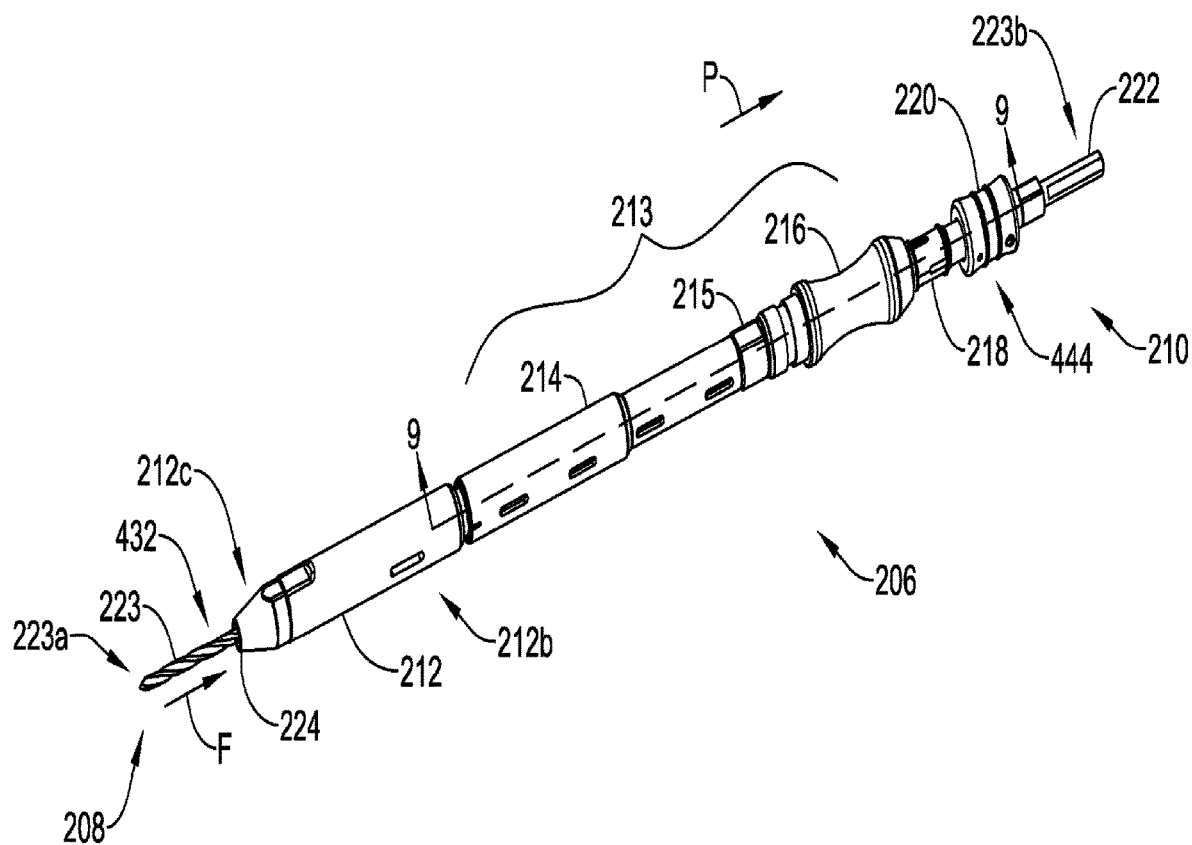
FIG. 8 is a schematic perspective view of an illustrative surgical bone drill bit assembly with a lock actuator secured in an unlock position and a shield withdrawn.
Figure 9:
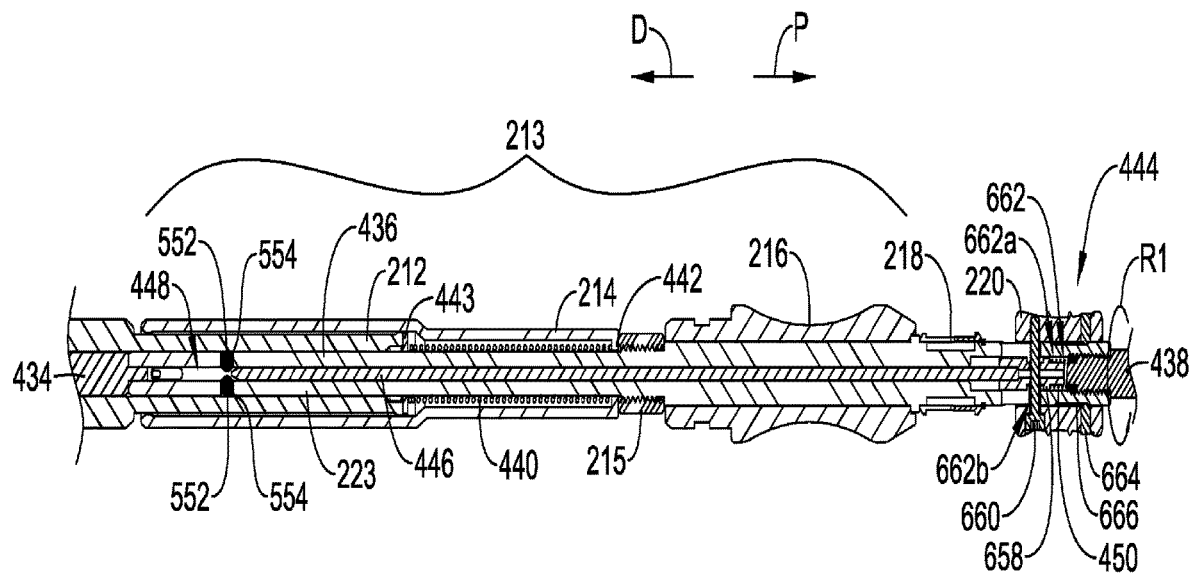
FIG. 9 is a schematic cross-sectional view of the illustrative bone drill bit assembly of FIG. 8, taken along line 9-9.

FIGS. 8 and 9 depict the drill bit assembly 206 with the lock actuator 220 in an unlock position (e.g., the locking system 444 is in the shield unlock position) and the shield 212 has been withdrawn such that the drill bit 223 and the cutting portion 432 thereof is exposed. As depicted in FIG. 8, the lock actuator 220 has been withdrawn and secured in the lock position, in a manner discussed herein or otherwise, such that the locking system 444 is in the shield unlock position. With the locking system 444 in the shield unlock position, the shield is able to withdraw in the proximal direction P and has withdrawn in the proximal direction P relative to the distal end portion 223a of the drill bit 223 in response to a force F acting on the shield 212 in the proximal direction P, where the force F is greater than a bias force of the first spring 440 acting on the shield 212 in the distal direction D.

FIG. 9 depicts a schematic partial cross-sectional view of the configuration of the drill bit assembly 206 depicted in FIG. 8, taken along line 9-9. As discussed, the locking system 444 has been adjusted to the shield unlock position in response to the lock actuator 220 being secured in the unlock position. As such, the lock actuator 220, the connector 660, the connector component 658, and the elongated member 446 have been moved in the proximal direction P and rotated in the rotational direction R1. The proximal positioning of the lock actuator 220 may result in the second spring 450 being compressed between the connector component 658 and the drill bit 223 (e.g., the third component 438) or between other suitable components of the drill bit assembly 206. Further, in response to withdrawing the elongated member 446, the balls 552 may be able to move freely within the openings 554 and the lumen 448 at the axial locations of the openings 554.

When the locking system 444 is in the shield unlock position and the bias force of the first spring 440 has been overcome, the shield 212 may withdraw with respect to the distal end portion 223a of the drill bit 223. As depicted in FIG. 9, when the shield 212 withdraws, the shield 212 may engage the balls 552 and force the balls 552 into the openings 554 and the lumen 448, and compress the first spring 440 between the shield 212 (e.g., the cap 443 of or on the shield 212) and the interior ledge 442. When the force F is removed or lessened to a level below the bias force of the first spring 440, the bias force of the first spring 440 may cause the shield 212 to move or extend in the distal direction D relative to the drill bit 223 to cover distal end portion 223a thereof.

Figure 10:
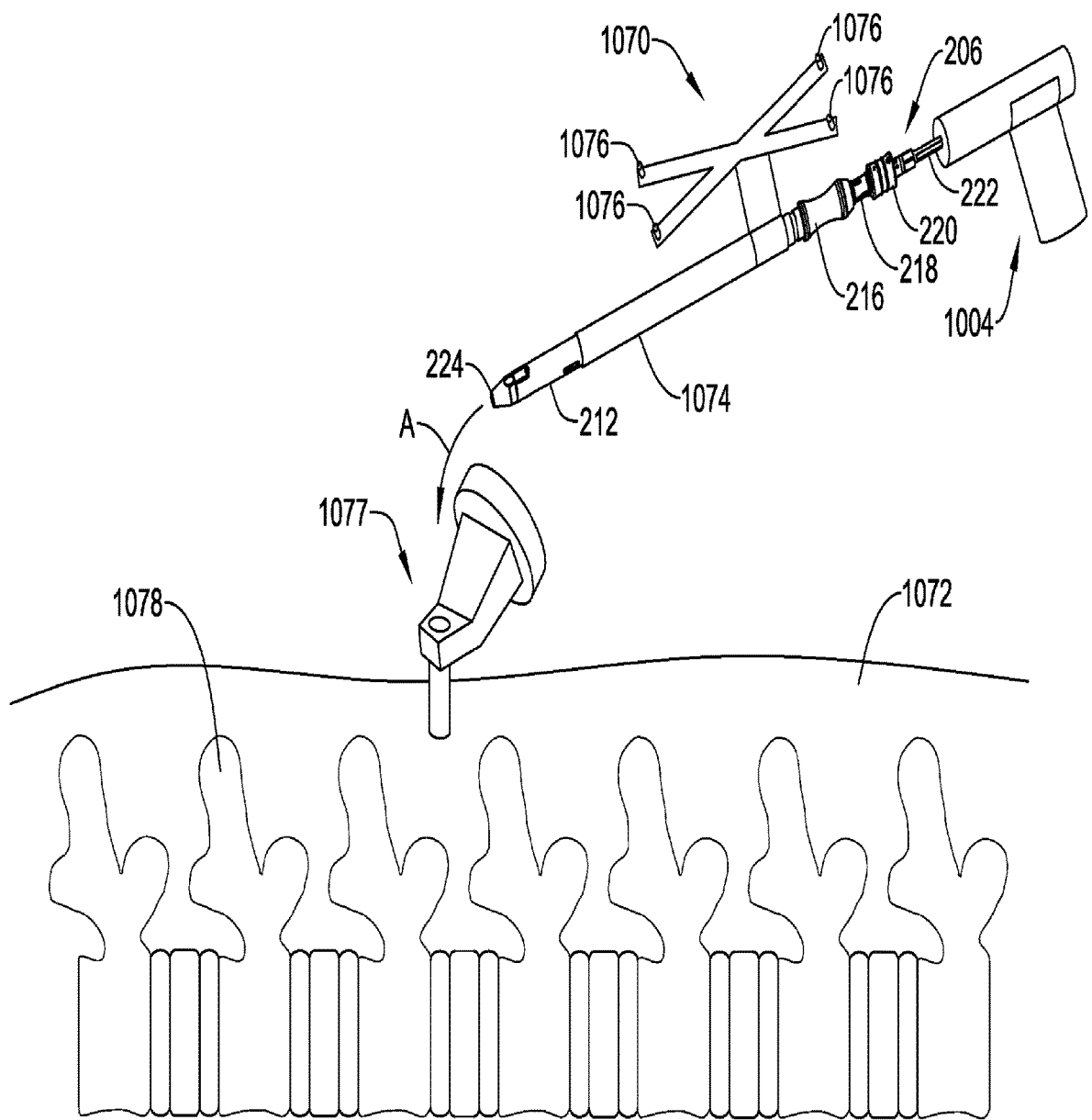
FIG. 10 is a schematic view of an illustrative surgical bone drill system for use in a procedure.

FIG. 10 is a schematic view of a surgical setup using the drill bit assembly 206. As depicted in FIG. 10, the drill bit assembly 206 has been inserted into and engaged with a drill 1004 and a navigational sleeve 1070, while the locking system 444 is in the shield lock position. The drill 1004 may be configured to engage the drill bit assembly 206 and rotate the drill bit (not shown) after the drill bit assembly 206 has been inserted into a subject 1072. Although not shown, a neuromonitoring clip may be connected to the neuromonitoring connection location 218 of the drill bit assembly 206 to facilitate using the drill bit assembly 206 to monitor target tissue and tissue around the target.

The navigational sleeve 1070 may include a sleeve component 1074 defining a lumen configured to receive drill bit 223 and the drill bit assembly 206 (e.g., the shield 212 and other components of the drill bit assembly 206) and one or more sense elements 1076 in a known position and configuration relative to the received drill bit assembly 206 such that a navigation system in a procedure room may sense the sense elements 1076. For example, the sense elements 1076 may be infrared emitters or retroreflective spheres detectable by the navigation system. Based on sensing the sense elements and the known position and configuration of the sensed elements relative to the drill bit assembly 206, the navigation system may determine a position of the drill bit assembly 206 or components thereof, and facilitate navigating the drill bit assembly 206 to and at a target location (e.g., a location in the subject 1072 at which to drill a hole or implant an implant).

Once the drill bit assembly 206 has been inserted into the navigational sleeve 1070, the drill bit assembly 206 in the navigational sleeve 1070 and connected to the drill 1004 may be inserted in the direction of arrow A into a surgical access tube 1077 to a surgical site (e.g., at the subject's vertebra 1078 or other target location). The surgical access tube 1077 may be held by a robotic arm, but this is not required. In some cases, a user (e.g., a surgeon or other suitable medical professional) may grip the drill 1004 with one hand and grasp the contoured portion 216 of the drill bit assembly 206 with two digits of a second hand, but this is not required, as the user inserts the drill bit assembly 206 into the surgical access tube 1077. Once at the surgical site, the user may engage the terminal tip 224 of the drill bit assembly 206 with a target bone, adjust the lock actuator 220 to the unlock position, secure the lock actuator 220 in the unlock position, and begin drilling a hole in the target bone, optionally using assistance from the surgical navigation system, the neuromonitoring system, or both. The surgical access tube 1077 may constrain a positioning of the drill bit 223 and the drill bit assembly 206 while the drill bit 223 is advanced into the target bone.

Figure 11:
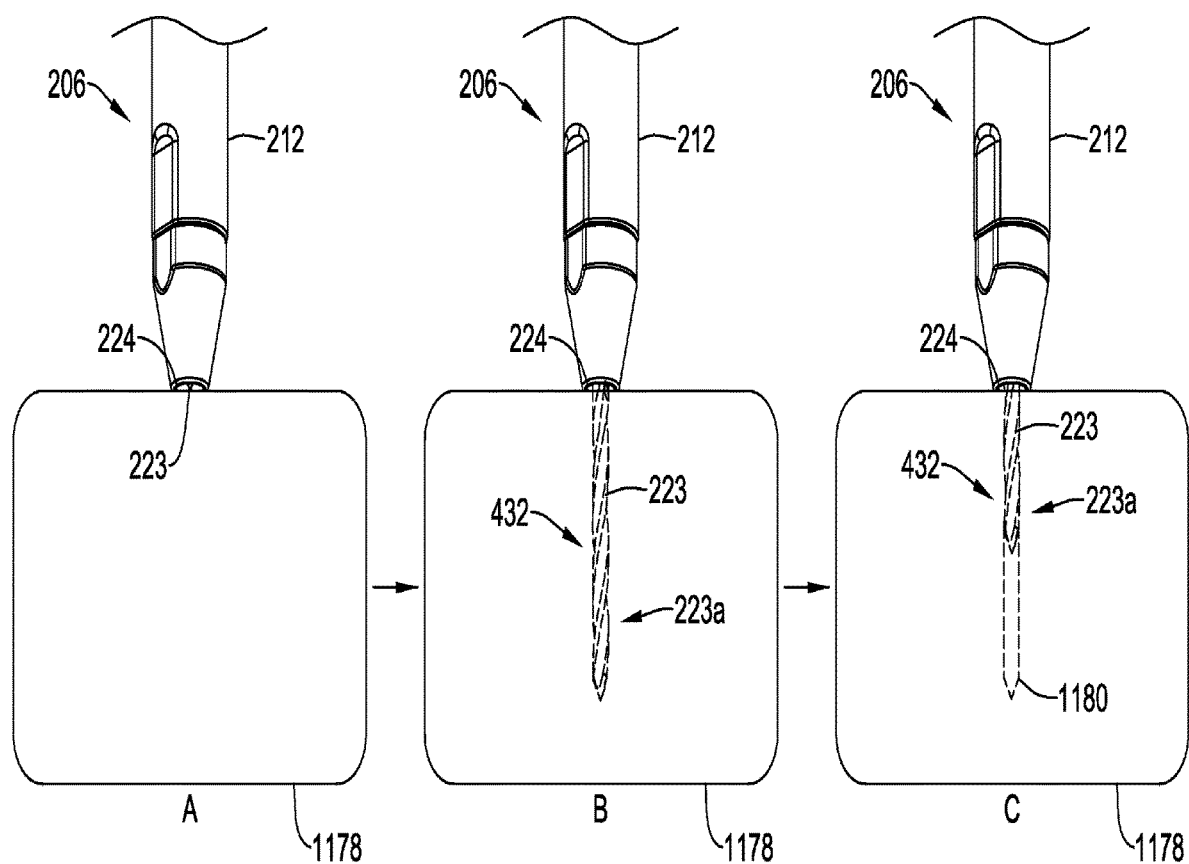
FIG. 11 is a schematic flow diagram of an illustrative use of a surgical bone drill bit assembly.

FIG. 11 is a schematic diagram depicting illustrative steps of using the drill bit assembly 206 to drill a hole (e.g., a pilot hole for a pedicle screw or other suitable hole) into a vertebra 1178 of a subject. At step A, the shield 212 (e.g., the terminal tip 224) of the drill bit assembly 206 may be brought into contact with the vertebra 1178 (e.g., a target bone of the subject). As discussed herein, the shield 212 may provide electrical insulation and act as a cutting guard for the drill bit 223.

At step B, a drill connected to the drill bit assembly 206 may initiate rotation of the drill bit 223 and the cutting portion 432 of the drill bit 223 may drill into the vertebra 1178, which may allow electrical stimulation from a conductive path through the drill bit 223 to be applied to the vertebra 1178 and surrounding tissue for neuromonitoring or other purposes. As the drill bit 223 drills into the vertebra 1178, the shield 212 may remain in contact with the vertebra 1178 and retract or withdraw relative to the distal end portion 223a of the drill bit, as shown in step B of FIG. 11.

At step C, the drill may cause the drill bit 223 to stop rotating or reverse rotation to facilitate withdrawal of the drill bit 223 from a hole 1180 in the vertebra 1178 formed by the drill bit 223. As the drill bit 223 withdraws or retracts from the hole 1180, the shield 212 may extend distally over the cutting portion 432 of the drill bit 223 and maintain contact with the vertebra 1178 to shield surrounding tissue from the drill bit 223. Once the drill bit 223 has been fully retracted from the vertebra 1178, the shield 212 may extend over an entirety of the drill bit 223 to cover the cutting portion 432 of the drill bit 223 and electrically insulate a conducive path through the drill bit 223 as the drill bit assembly 206 is withdrawn from the subject.

Figure 12:
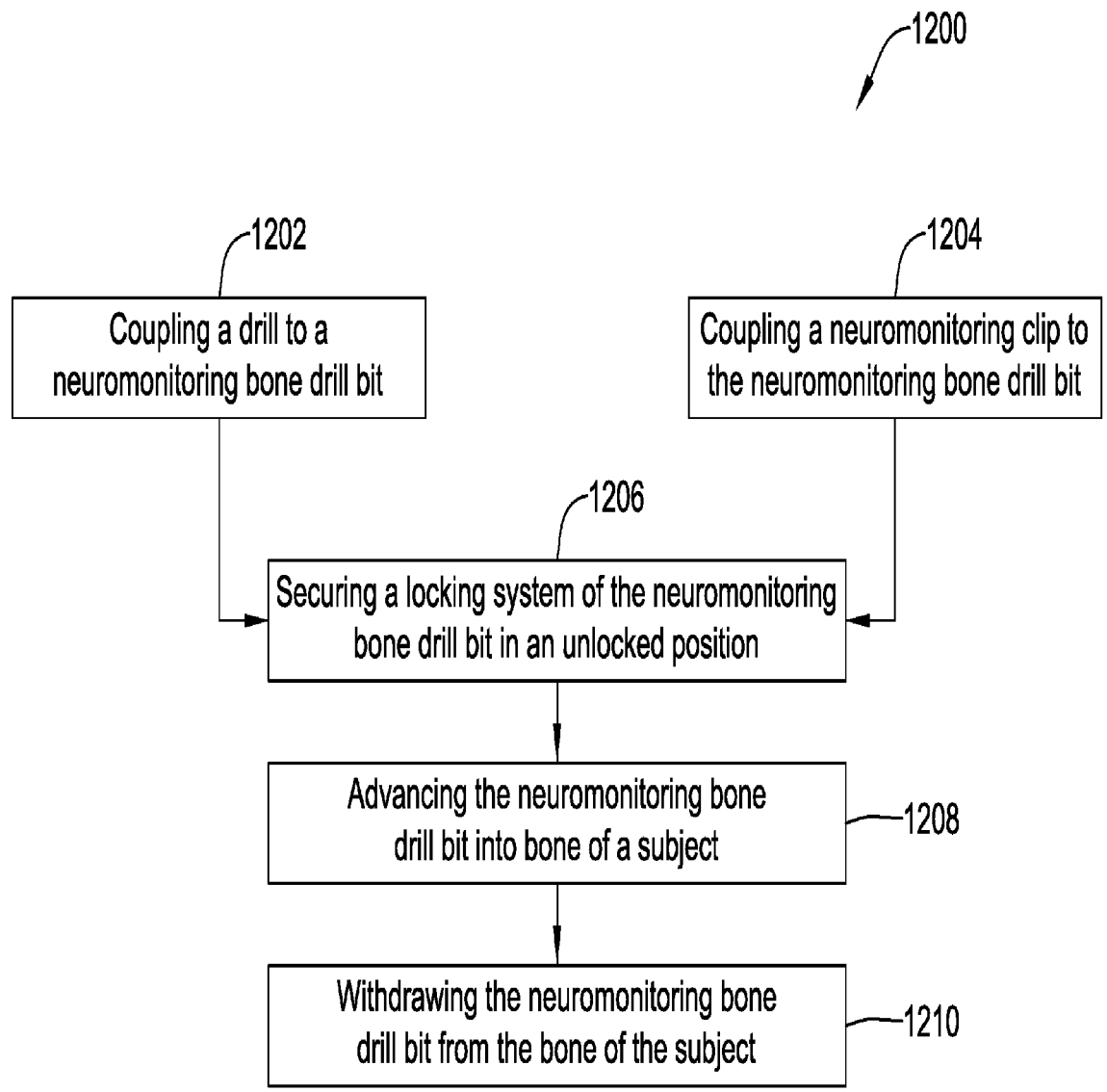
FIG. 12 is a schematic flow diagram of an illustrative method of using a surgical bone drill system.

FIG. 12 depicts an illustrative method 1200 of using the drill bit assembly 206 to drill a hole (e.g., a pilot hole for a pedicle screw or other hole) into a bone (e.g., vertebra or other bone tissue) of a subject. The method may include coupling 1202 a drill 104 to a neuromonitoring bone drill bit 223 or other suitable surgical bone drill bit. In some cases, the neuromonitoring bone drill bit 223 may include an electrically insulating shield 212 and a cover 214 extending over the neuromonitoring bone drill bit, which may be part of the drill bit assembly 206, as discussed herein. The drill 104 may be coupled to the neuromonitoring bone drill bit 223 in any suitable manner for coupling drills and drill bits. In some cases, the drill may grasp or engage the drill bit shank 222 of the neuromonitoring bone drill bit 223.

Further, the method 1200 may include coupling 1204 a neuromonitoring clip to the bone drill bit. In some cases, the neuromonitoring clip may be applied to the neuromonitoring connection portion 218 of the drill bit assembly 206, where the neuromonitoring connection portion 218 is in electrical communication with the neuromonitoring bone drill bit 223.

The neuromonitoring clip may be connected to the drill bit assembly 206 in any suitable manner. In one example, the neuromonitoring clip (e.g., a spring-loaded metallic clip or other suitable neuromonitoring clip) may be electrically and mechanically coupled to the neuromonitoring connection portion 218 such that the neuromonitoring bone drill bit 223 may rotate relative to the neuromonitoring clip, but this is not required and the neuromonitoring clip may be electrically coupled to the neuromonitoring bone drill bit 223 in one or more other suitable manners. In other examples, the neuromonitoring clip may be mechanically coupled directly to the neuromonitoring bone drill bit 223 or to the drill (e.g., the drill 104) to create an electrical coupling between the neuromonitoring clip and the drill bit 223.

Once the neuromonitoring bone drill bit 223 is connected to the drill 104 and the neuromonitoring clip is coupled to the neuromonitoring bone drill bit 223, the neuromonitoring bone drill bit 223 may be inserted into a surgical site at a bone (e.g., a target bone) of the subject. The neuromonitoring bone drill bit 223 any be inserted into the surgical site in any suitable manner. In one example, as discussed herein, the neuromonitoring bone drill bit 223 may be inserted into the surgical site with a locking system 444 of the drill bit assembly 206 in a locked position in which an electrically insulating shield 212 is not able to retract or withdraw from a position at which the electrically insulating shield 212 is covering the distal end portion 223a of the neuromonitoring bone drill bit 223 to insulate a conductive path through the neuromonitoring bone drill bit 223. Further, in some cases, the neuromonitoring bone drill bit 223 may be inserted into the surgical site by disposing the neuromonitoring bone drill bit 223 in a surgical access tube 1077 (e.g., a guide tube) held by a robotic arm or other secure support. The surgical access tube 1077 may constrain positioning of the neuromonitoring bone drill bit 223 while the neuromonitoring bone drill bit 223 is advanced into the bone of the subject.

The method 1200 may further include securing 1206 a locking system 444 of the drill bit assembly 206 including the neuromonitoring bone drill bit 223 in an unlocked position (e.g., the shield unlock position), for example, after the neuromonitoring bone drill bit 223 has been inserted to a surgical site. In one example when utilizing the drill bit assembly 206, the locking system 444 may be adjusted to and secured in the unlocked position by moving (e.g., proximally withdrawing or otherwise moving) the lock actuator 220 to an unlock position and rotating the lock actuator 220 to secure the lock actuator 220 in the unlock position. The locking system 444 may be secured in the unlocked position in one or more other suitable manners. Securing the locking system 444 in the unlocked position may allow the electrically insulating shield 212 to withdraw proximally in response to engagement of the electrically insulating shield 212 with tissue of the subject.

Once the locking system 444 has been secured in the unlocked position, the neuromonitoring bone drill bit 223 may be advanced 1208 into the bone of the subject. The neuromonitoring bone drill bit 223 may be advanced into the bone by a user causing the drill 104 to rotate the neuromonitoring bone drill bit 223 and the user applying a force to the drill 104. Advancing the neuromonitoring bone drill bit 223 into tissue of the subject may cause the electrically insulating shield 212 to engage the tissue and result in the electrically insulating shield 212 withdrawing proximally relative to the distal end portion 223a as the neuromonitoring bone drill bit 223 advances into the tissue of the subject. Although other configurations are contemplated, the electrically insulating shield 212 may be configured to retract or withdraw in the manners discussed herein.

In some cases, as the neuromonitoring bone drill bit 223 is advanced into the bone of the subject, an electrical stimulation may be applied to the bone by electrically stimulating the neuromonitoring bone drill bit 223 with the neuromonitoring clip coupled thereto. Further, a neuromonitoring system may monitor the electrical stimulation or the subject's response to the electrical stimulation for responses to the electrically stimulation that are indicative of a pedicle breach. Further, the electrical stimulations may be monitored for one or more other suitable purposes.

After advancing the neuromonitoring bone drill bit 223 into tissue of the subject, the neuromonitoring bone drill bit 223 may be withdrawn 1210 from the tissue of the subject. In some cases, as the neuromonitoring bone drill bit 223 is withdrawn from the tissue of the subject, the electrically insulating shield 212 may automatically advance distally over the distal end portion 223a of the neuromonitoring bone drill bit 223 in the manners discussed herein or in other manners. The electrically insulating shield 212 covering the distal end portion 223a of the neuromonitoring bone drill bit 223 during and after withdrawal of the neuromonitoring bone drill bit 223 from the subject's tissue may facilitate electrically insulating the neuromonitoring bone drill bit 223 as the neuromonitoring bone drill bit 223 is withdrawn from the subject.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, or characteristics. However, such recitations do not necessarily mean that all embodiments include the particular features, structures, or characteristics. Additionally, when particular features, structures, or characteristics are described in connection with one embodiment, it should be understood that such features, structures, or characteristics may also be used connection with other embodiments whether or not explicitly described unless clearly stated to the contrary.

The above detailed description should be read with reference to the drawings in which similar elements in different drawings are numbered the same. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method comprising:
   providing a surgical assembly including:
   a surgical bone drill bit having a distal end portion and a proximal end portion,
   a neuromonitoring connection in electrical communication with the surgical bone drill bit,
   a shield extending over the distal end portion of the surgical bone drill bit, and
   a locking system in communication with the shield, wherein the locking system is biased to a shield lock position and is configured to be secured in a shield unlock position relative to the surgical bone drill bit; and
   advancing the surgical bone drill bit into bone of a subject, wherein advancing the surgical bone drill bit into the bone of the subject causes the shield to withdraw proximally relative to the distal end portion as the surgical bone drill bit advances into the bone of the subject.

2. The method of claim 1, wherein the shield is biased toward a distal end of the surgical bone drill bit.

3. The method of claim 1, wherein the shield includes teeth at a distal end of the shield.

4. The method of claim 1, wherein the locking system further includes:
   an elongated member;
   a lock actuator configured to engage the elongated member and slide along the surgical bone drill bit; and
   one or more balls; and
   wherein the lock actuator has a lock position associated with the shield lock position and an unlock position associated with the shield unlock position and is configured to be secured in the unlock position.

5. The method of claim 4, wherein the surgical bone drill bit has a lumen having one or more openings at an axial location along the lumen, the one or more openings being configured to receive the one or more balls.

6. The method of claim 5, wherein the surgical assembly is configured such that the elongated member translates axially along the lumen when the lock actuator is actuated from the lock position to the unlock position to allow the shield to withdraw proximally.

7. The method of claim 5, wherein when the lock actuator is at the lock position to prevent the shield from withdrawing proximally, the elongated member extends within the lumen and positions the one or more balls within the one or more openings such that the one or more balls extend exterior of the surgical bone drill bit.

8. The method of claim 5, wherein a proximal end of the shield includes a taper configured to drive the one or more balls into the one or more openings and the lumen as the shield withdraws proximally.

9. The method of claim 5, wherein the surgical assembly is configured such that inertia of the surgical bone drill bit rotating causes the lock actuator to transition from the unlock position to the lock position once drilling stops or the surgical bone drill bit is reversed.

10. The method of claim 1, wherein the surgical assembly further includes:
    a drill bit sleeve extending along at least a portion of the surgical bone drill bit,
    wherein the drill bit sleeve and the shield electrically insulate a conductive path extending from the neuromonitoring connection to a distal end of the surgical bone drill bit; and
    wherein the drill bit sleeve is configured to receive a portion of the shield as the shield withdraws proximally.

11. The method of claim 10, wherein the surgical bone drill bit is configured to rotate relative to the drill bit sleeve and the shield.

12. A method comprising:
    providing a surgical system including:
    a surgical bone drill bit having a distal end portion and a proximal end portion,
    a drill configured to receive the proximal end portion of the surgical bone drill bit,
    a neuromonitoring clip connected to a neuromonitoring connection on the surgical bone drill bit,
    a shield extending over the distal end portion of the surgical bone drill bit, and
    a locking system in communication with the shield, wherein the locking system is biased to a lock position at which the shield is prevented from sliding along the distal end portion of the surgical bone drill bit, and wherein the locking system is configured to be secured in an unlocked position relative to the surgical bone drill bit at which the shield is able to slide along the distal end portion of the surgical bone drill bit; and
    advancing the surgical bone drill bit into bone of a subject, wherein advancing the surgical bone drill bit into the bone of the subject causes the shield to withdraw proximally relative to the distal end portion as the surgical bone drill bit advances into the bone of the subject.

13. The method of claim 12, wherein the surgical system further includes:
    a drill bit sleeve extending over the surgical bone drill bit at a location proximal to the shield, and
    wherein the drill bit sleeve is configured to receive the shield as the shield slides along the distal end portion of the surgical bone drill bit.

14. The method of claim 13, wherein the drill bit sleeve includes a concave contoured portion configured for receiving a user's grip and the surgical bone drill bit is configured to rotate with respect to the concave contoured portion of the drill bit sleeve.

15. The method of claim 12, wherein the surgical system further includes:
a navigable surgical sleeve; and
wherein the navigable surgical sleeve defines a lumen configured to receive the surgical bone drill bit and the shield extending over the distal end portion of the surgical bone drill bit.

16. The method of claim 12, further comprising:
withdrawing the surgical bone drill bit from the bone of the subject, wherein withdrawing the surgical bone drill bit from the tissue of the subject causes the shield to advance distally over the distal end portion of the neuromonitoring bone drill bit.

17. The method of claim 16, further comprising:
electrically stimulating the surgical bone drill bit with the neuromonitoring clip; and
monitoring for a response to the stimulating indicative of a pedicle breach.

18. The method of claim 16, further comprising:
disposing the surgical bone drill bit in a guide tube held by a robotic arm, and
wherein the guide tube constrains positioning of the surgical bone drill bit while the neuromonitoring bone drill bit is advanced into the bone of the subject.

\* \* \* \* \*